United States Patent [19]

Kikuchi et al.

[11] 4,185,119
[45] Jan. 22, 1980

[54] ANTIALLERGIC METHODS

[75] Inventors: Hiroyuki Kikuchi, Tokyo; Nobuo Kawaguchi, Kokubunji; Hideaki Shiokawa, Asaka, all of Japan

[73] Assignee: Fujisawa Pharmaceutical Co., Ltd., Osaka, Japan

[21] Appl. No.: 910,511

[22] Filed: May 30, 1978

[30] Foreign Application Priority Data

May 30, 1977 [JP] Japan .................................. 52-63739

[51] Int. Cl.² ............................................ A61K 31/47
[52] U.S. Cl. ..................................................... 424/258
[58] Field of Search ........................................ 424/258

[56] References Cited

PUBLICATIONS

Chemical Abstracts 68: 94521z, (1968).
Merck Index, 9th Ed., p. 172, (1339), (1976).

Primary Examiner—Leonard Schenkman
Attorney, Agent, or Firm—Oblon, Fisher, Spivak, McClelland & Maier

[57] ABSTRACT

Compounds of the formula:

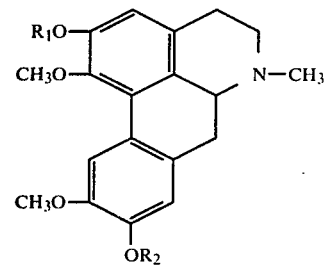

wherein $R_1$ and $R_2$ are each hydrogen or methyl, providing that when $R_1$ is hydrogen, $R_2$ is hydrogen, have been found to be useful in relieving allergic symptoms by inhibiting histamine-release from mast cells. They can be used in free form or in the form of pharmaceutically acceptable acid addition salts.

6 Claims, No Drawings

ANTIALLERGIC METHODS

This invention relates to novel use of a compound of the formula:

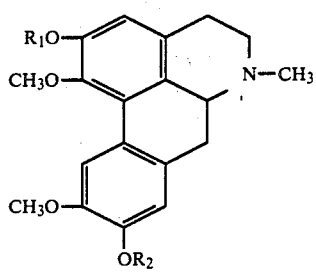

wherein $R_1$ and $R_2$ are each hydrogen or methyl, providing that when $R_1$ is hydrogen, $R_2$ is hydrogen.

More particularly, it relates to use of the compound (I) as antiallergic agent for prophylaxis and therapy to mammals, to method for treating allergic diseases by administering the compound (I) by itself or in a pharmaceutical form thereof and also to pharmaceutical composition useful as antiallergic agent which comprises one or more compound(s) selected from the group represented by the compound (I).

The compound (I) per se is known and disclosed in the publications, e.g. BERICHTE DER DEUTSCHEN CHEMISHEN GESELLSCHAFT Vol. 66, Page 1344 (1933) which discloses N-methyllaurotetanine, i.e., the compound (I) wherein $R_1$ is methyl and $R_2$ is hydrogen; Journal of the Chemical Society Page 4478 (1964) which discloses glaucine, i.e., the compound (I) wherein $R_1$ and $R_2$ are both methyl; and YAKUGAKUZASSHI Vol. 86, Page 129 (1966) which discloses boldine, i.e., the compound (I) wherein $R_1$ and $R_2$ are both hydrogen. As to pharmacological properties of the compound (I) also, it is publicly known that N-methyllaurotetanine possesses a curariform activity as disclosed in Japanese Patent Publication No. 24092/1961, glaucine possesses an adrenolytic action and antitussive properties as disclosed in Chemical Abstracts Vol. 68, 94521Z (1968) and boldine possesses a diuretic activity as disclosed in THE MERCK INDEX EIGHTH EDITION, Page 159 (1968).

As results of extensive studies, the inventors of this invention have newly found out that the compound (I) possesses an attractive pharmacological activity i.e. desirable and superior antiallergic activity. This finding prompts the inventors to make the more intensive studies on the compound (I) and have resulted in providing this invention.

It is interesting that the compound (I) exhibits an excellent activity for inhibition of histamine-release from most cells, which is concerned with allergic symptoms in mammals. This activity is a novel pharmacological property of the compound (I) and is pharmacologically different from those as disclosed in the prior arts mentioned above.

Accordingly, an object of this invention is to provide a method for using the compound (I), a pharmaceutically acceptable acid addition salt thereof or a pharmaceutical composition thereof to relieve symptoms associated with allergic diseases such as Allergic asthma, Allergic rhinitis, Urticaria, Pollenosis, Allergic conjunctivitis, Atopic dermatitis, Ulcerative colitis, Alimentary allergy (e.g. Milk allergy), Bird fancier's disease, Aphthous stomatitis and the like.

Another object of this invention is to provide a method for treating allergic diseases to prevent or relieve the symptoms.

Further object of this invention is to provide an antiallergic composition for oral or parenteral use.

The compound (I) can be used as an active antiallergic agent either in the free form or in the form of the pharmaceutically acceptable acid addition salt thereof such as a salt with inorganic acid (e.g. hydrochloric acid, hydrobromic acid, sulfuric acid, phosphoric acid, etc.) and a salt with organic acid (e.g. citric acid, lactic acid, oxalic acid, malic acid, salicyclic acid, maleic acid, etc.). These acid addition salts can be prepared in a conventional manner.

An active ingredient, i.e. the compound (I) or its pharmaceutically acceptable acid addition salt, or pharmaceutical compositions comprising the same can be administered to mammals including human being in a conventional pharmaceutical form such as capsules, micro-capsules, tablets, granules, powders, troches, pills, ointments, suppositories, injectable solutions, syrups, aerosols, inhalations, etc. And an effective amount thereof for the prophylaxis or therapy is not accompanied with any undesired side effects and so much severe toxicity.

The pharmaceutical compositions of this invention can contain various organic or inorganic carrier materials, which are conventionally used for pharmaceutical purpose, such as excipient (e.g. sucrose, starch, mannit, sorbit, lactose, glucose, cellulose, talc, calcium, phosphate, calcium carbonate, etc.), binding agent (cellulose, methyl cellulose, hydroxypropylcellulose, polypropylpyrrolidone, gelatin, gum arabic, polyethyleneglycol, sucrose, starch, etc.), disintegrator (e.g. starch, carboxymethyl cellulose, calcium salt of carboxymethyl cellulose, hydroxypropyl-starch, sodium glycolestarch, sodium bicarbonate, calcium phosphate, calcium citrate, etc.), lubricant (e.g. magnesium stearate, aerosil, talc, sodium laurylsulfate, etc.), flavoring agent (e.g. citric acid, mentol, ammonium salt of glycyrlysine, glycine, orange powders, etc.), preservative (sodium benzoate, sodium bisulfite, methylparaben, propylparaben, etc.), stabilizer (citric acid, sodium citrate, acetic acid, etc.), suspending agent (e.g. methyl cellulose, polyvinylpyrrolidone, aluminum stearate, etc.), dispersing agent [e.g. polysorbate 80, emalgen 408 (surface active agent), emasol (surface active agent), etc.], aqueous diluting agent (e.g. water), base wax (e.g. cacao butter, polyethyleneglycol, witepsol, white petrolatum, etc.).

A dosage of the present active ingredient is to be varied depending on various factors such as weight and/or age of a patient and/or a stage of the allergic disease, and further the kind of administration route. In general, an effective dosage may be in a range of about 20-2000 mg/day for an oral route, about 2.5-250 mg/day for an intramuscular or intravenous injection, about 10-1000 mg/day for a subcutaneous injection and about 120 mg-2000 mg/day for a rectal route. The total daily amount mentioned above may be divisionally given to the patient at the interval of 6-12 hours per day. Preferable single dose of the present active ingredient may be, for example, about 10-500 mg per tablet or capsule, about 1.25-250 mg per vial or ampoule, or about 60-500 mg per suppository, and so on, and further a pharmaceutical form for an external use may be, for example, about 1–10% ointment, solution or emulsion, etc.

The following Tests are given for illustrating pharmacological activities of the compound (I) of this invention.

Test: Acute Toxicity in Mice

A normal saline containing each of the test compound mentioned below and 0.5% carboxymethylcellulose was given intraperitoneally to male I.C.R. (Institute of Cancer Research) strain mice aged 5 weeks, weighing 33–35 g. $LD_{50}$ values were calculated from the survivals of mice at one week after the administratio of the test compound.

The results thus obtained are shown in the following table.

| Test (Compound | $LD_{50}$ (mg/kg) |
|---|---|
| N-Methyllaurotetanine hydrochloride | 91.65 |
| Glaucine | 211.9 |
| Boldine | 145.2 |

Test: Side Effects (i) Rotational behavior inducing action in rats unilaterally lesioned in substantia nigra,
(ii) Gnawing behavior including action in rats, and
(iii) Vomiting-inducing action in dogs The tests for the above actions of the compound (I) were conducted by using apomorphine as a control and revealed that the compound (I) has no side effect as above.

Test: Antiallergic Action (1) Preparation of antiserum (a) Rat reaginic antiserum against egg albumin A solution of egg albumin (2 mg) in B. pertussis-diphtheria-tetanus mixed vaccine (1 ml.) (made by Takeda Chemical Industries Ltd.) was mixed with an equal volume of incomplete adjuvant (made by Difco Laboratories) to give an emulsion. The emulsion was given subcutaneously in a single dose of 1 ml. divided equally (0.25 ml.) to the four foot pads of male S.D. (Sprague-Dawley) strain rats aged 8 weeks, each weighing about 300 g.

Five days after the ad ninistration, a solution of egg albumin (0.5 mg.) in B. pertussis-diphtheria-tetanus mixed vaccine (0.5 ml.) was further given intramuscularly in a single dose of 0.5 ml. divided equally (0.25 ml.) to 2 places of thigh of the same rats.

Three days after the second administration, blood samples were collected from femoral artery of the rats and allowed to stand at ambient temperature for 5 hours. The separated supernatant was centrifuged at 4° C. (10,000 r.p.m.×1 hour). The antisera thus obtained were stored at −80° C. prior to use.

(b) Rat hyperimmune antiserum against egg albumin

A solution of egg albumin (20 mg.) in normal saline (1 ml.) was mixed with complete adjuvant (1 ml.) (made by Difco Laboratories) to given an emulsion. The emulsion was subcutaneously given in a single dose of 1 ml. divided equally (0.25 ml.) to the four pads of male S.D. strain rats aged 6 weeks, each weighing about 200 g. (The first immunization).

One week after the administration, an emulsion which was prepared by mixing a solution of egg albumin (10 mg.) in normal saline (1 ml.) with complete adjuvant (1 ml.) was further given subcutaneously (at 3 places) and intramuscularly (at 1 place) in a single dose of 1 ml. divided equally (0.25 ml.) to thigh of the same rats. (The second immunization).

Three weeks after the second administration, a solution of egg albumin (1 mg.) in normal saline (1 ml.) was further given intracutaneously in a single dose of 0.3 ml. divided equally (0.1 ml.) to 3 places of the same rats. (The third immunization).

One week after the third administration, blood samples were collected from rats and treated in substantially the same manner as described in the above item (a). The antisera thus obtained were stored at −80° C. prior to use.

(c) Guinea-pig antiserum against egg albumin

A solution of egg albumin (10 mg.) in normal saline (1 ml.) was mixed with incomplete adjuvant (1 ml.) to give an emulsion. The emulsion was given subcutaneously in a single dose of 0.4 ml. divided equally (0.1 ml.) to the four pads of male Hartley strain guinea-pigs, each weighing 350–380 g.

Two weeks after the administration, a solution of egg albumin (1 mg.) in normal saline (1 ml.) was further given subcutaneously in a single dose of 0.4 ml divided equally (0.1 ml.) to the four pads of the same guinea-pigs.

Subsequently, one week and two weeks after the second adminstration, the guinea-pigs were treated in substantially the same manner as the above second administration.

One week after the final administration, blood samples were collected from the guinea-pigs and treated in substantially the same manner as described in the above item (a). The antisera thus obtained were stored at −80° C. prior to use.

(2) Inhibition test of P.C.A. (Passive Cutaneous Anaphylaxis) reaction (a) Inhibitory effect on P.C.A. reaction in S.D. strain rats Fifteen male S.D. strain rats aged 8 weeks, each weighing about 270 g were divided equally into 3 groups.

A rat reaginic antiserum (0.07 ml.) as prepared by the above (1)-(a) was given intracutaneously to the depilated back of each rat of Group I and Group II. On the other hand, a rat normal serum (0.07 ml.) was given intracutaneously to the depilated back of each rat of Group III, respectively.

Thirty hours after the administration, a normal saline (0.5 ml.) containing egg albumin (7.5 mg.) and Evans blue (2.5 mg.) was intravenously given to each rat of Groups I–III in order to bring about P.C.A., respectively.

Beforehand, 3 hours, 1 hour and 30 seconds before the intravenous administration to bring about P.C.A., a normal saline (1 ml.) containing the prescribed amount of N-methyllaurotetanine hydrochloride and carboxymethylcellulose (0.5 %) was given orally, intraperitoneally or intravenously to each rat of Group I and a normal saline (1 ml.) containing only carboxymethylcellulose (0.5% was also given orally, intraperitoneally or intravenously to each rat of Group II.

Thirty minutes after challenge with antigen, the animals were sacrificed and then skinned. To each of the sensitized spots punched, was added a mixture (7 ml.) of acetone and 2% aqueous sodium alkylbenzenesulfonate solution (4:1) and then the mixture was homogenized. The homogenate was shaken at ambient temperature for 2 hours and filtered. Optical density at 620 nm of the filtrate was determined and from the value of the optical density, inhibitory effect of P.C.A. reaction was calculated by using the following equation.

$$\text{Inhibitory effect (\%) on P.C.A. reaction} = \left(1 - \frac{B-C}{A-C}\right) \times 100$$

A: Optical Density Value of Group II
B: Optical Density Value of Group I
C: Optical Density Value of Group III Further, an inhibition test on P.C.A. reaction using the rat hyperimmuneantiserum against egg albumin was carried out in substantially the same manner as described in the above, excepting that the intravenous administration to bring about P.C.A. was carried out at 5.5 hours after the administration of the serum and antiserum. And inhibitory effect on the P.C.A. reaction was also calculated in substantially the same manner as described in the above.

The results thus obtained are shown in the following Table 1.

Table 1

| Administration route of the test compound | Dose (mg/kg) of the test compound | Inhibitory effect on P.C.A. reaction in S.D. strain rat | | | |
|---|---|---|---|---|---|
| | | Rat reaginic antiserum against egg albumin | | Rat hyperimmune antiserum against egg albumin | |
| | | Inhibitory effect on P.C.A. reaction (%) | $ED_{50}$ (mg/kg) | Inhibitory effect on P.C.A. reaction (%) | $ED_{50}$ (mg/kg) |
| Oral | 200 | 85 | | 81 | |
| | 66 | 35 | 100 | 33 | 110 |
| | 20 | 16 | | 42 | |
| Intraperitoneal | 40 | 85 | | 72 | |
| | 13 | 80 | 4.8 | 60 | 11 |
| | 4 | 6 | | 20 | |
| Intravenous | 9 | 85 | | 65 | |
| | 3 | 57 | 2.5 | 46 | 4 |
| | 1 | 24 | | 23 | |

(b) Inhibitory effect on P.C.A. reaction in Donryu strain rat

The following tests were carried out in substantially the same manner as described in the above item (2)-(a).

(i) Test compound: N:methyllaurotetanine hydrochloride
Test animal: Male Donryu strain rats aged 8 weeks, weighing about 130 g.
Challenge: A normal saline (0.3 ml.) containing egg albumin (4.5 mg.) and Evans blue (1.5 mg.).

The results are shown in the following Table 2-I.

Table 2-I

| Administration route of the compound | Dose (mg/kg) of the test compound | Inhibitory effect (1) on P.C.A. reaction in Donryu strain rats | |
|---|---|---|---|
| | | Inhibitory effect (%) | |
| | | Rat reaginic antiserum against egg albumin | Rat hyperimmune antiserum against egg albumin |
| Oral | 200 | 90 | 65 |
| | 66 | 70 | 40 |
| | 20 | 40 | 30 |
| Intraperitoneal | 40 | 70 | 50 |
| | 13 | 60 | 55 |
| | 4 | 30 | 10 |
| Intravenous | 20 | 100 | 80 |
| | 6.7 | 70 | 50 |

(ii) Test commpound: glaucine or boldine
Test animal: Male Donryu strain rats aged 8 weeks, weighing 140–150 g.
Challenge: the same as the above item (b)-(i).

The results are shown in the following Table 2-II.

Table 2-II

| Test compound (Administration route) | Dose of test compound (mg/kg) | Inhibitory effect (2) on P.C.A. reaction in Donryu strain rats | |
|---|---|---|---|
| | | Inhibitory effect (%) | |
| | | Rat reaginic antiserum against egg albumin | Rat hyperimmune antiserum against egg albumin |
| Glaucine (oral) | 200 | 95 | 90 |
| | 100 | 80 | 80 |
| | 50 | 70 | 60 |
| Glaucine (intraperitoneal) | 60 | 95 | 85 |
| | 20 | 60 | 50 |
| Boldine | 66 | 40 | 30 |

Table 2-II-continued

Inhibitory effect (2) on P.C.A. reaction in Donryu strain rats

| Test compound (Administration route) | Dose of test compound (mg/kg) | Inhibitory effect (%) | |
|---|---|---|---|
| | | Rat reaginic antiserum against egg albumin | Rat hyperimmune antiserum against egg albumin |
| (intraperitoneal) | | | |

(c) Inhibition test of P.C.A. reaction in I.C.R. (Institute of Cancer Research) strain mice (i) Test compound: N-methyllaurotetanine hydrochloride Fifteen male I.C.R. strain mice aged 7 weeks, weighing about 35 g were divided equally into 3 groups. Each of the groups was composed of 5 mice, (in case of intraperioneal administration of the test compound to the mouse, each of the groups was composed of 10 mice).

Ten-hold diluted solution (0.05 ml.) of the rat hyperimmune antiserum against egg albumin was given intracutaneously to the depilated back of each mouse of Group I and Group II, respectively. On the other hand, a rat normal serum (0.05 ml.) was given intracutaneously to the depilated back of each mouse of Group III. Three hours after the administration, a normal saline (0.1 ml.) containing egg albumin (1.5 mg.) and Evans blue (0.5 mg.) was given intravenously to each mouse of Groups I-III in order to bring about P.C.A., respectively.

Beforehand, 3 hours and 1 hours before the admnistration to bring about P.C.A., a normal saline (0.3 ml.) containing the prescribed amount of N-methyllaurotetanine hydrochloride and carboxymethylcellulose (0.5%) was given orally or intraperitoneally to each mouse of Group I, and a normal saline (0.3 ml.) containing only carboxymethylcellulose (0.5%) was given orally or intraperitoneally to each mouse of Group II.

The procedure followed by the above, was carried out in substantially the same manner as described in the above item (2)-(a).

The results are shown in the following Table 3-I.

Table 3-I

| | Inhibitory effect on P.C.A. reaction in I.C.R. mouse | |
|---|---|---|
| Administration Route | Dose of test compound (mg/kg) | Inhibitory effect (%) |
| Oral | 145 | 70 |
| | 48 | 50 |
| | 16 | 20 |
| Intraperitoneal | 30 | 95 |
| | 10 | 80 |
| | 3 | 50 |

(ii) Test compound: Glaucine and Boldine

Test animal: Male I.C.R. strain mice aged 6 weeks, weighing about 35 g.

This test was carried out in substantially the same manner as described in the above item (c)-(i).

The results are shown in the following Table 3-II.

Table 3-II

| | Inhibitory effect on P.C.A. reaction in I.C.R. strain mouse | |
|---|---|---|
| Test compound (Administration route) | Dose of the test compound (mg/kg) | Inhibitory effect (%) |
| Glaucine (Intraperitoneal) | 30 | 60 |
| | 10 | 50 |
| Boldine (Intraperitoneal) | 30 | 20 |

(3) Inhibition test of anaphylactic asthma in guinea-pigs

To ten male Hartley strain guinea-pigs, weighing 300 g was given intravenously the guinea-pig antiserum against egg albumin (0.1 ml.), respectively. Twenty four hours after the administration, each of the guinea-pigs was put individually into each of boxes (innercapacity: 5.3 liters). A normal saline containing egg albumine (1%) was continuously sprayed with a nebulizer into the boxes.

Beforehand, one hour and 30 seconds before putting the guinea-pigs into each of the boxes, a normal saline (1 ml.) containing the prescribed amount of N-methyllaurotetanine hydrochloride and carboxymethylcellulose (0.5%) was given intraperitoneally to five guinea-pigs and a normal saline (1 ml.) containing only carboxymethylcellulose (0.5%) was given intraperitoneally to each of the remaining 5 guinea-pigs. Time till the test animal was suffocated to death, was measured and when animals survived more than 7 minutes, inhibition of anaphylactic asthma were judged as effective. Survival (%) was calculated by the following formula:

$$\text{Survival (\%)} = \frac{\text{Number of animals survived more than 7 minutes}}{\text{Number of test animals}} \times 100$$

The results are shown in the following Table 4.

Table 4

| | Inhibitory effect on anaphylactic asthma in guinea-pig | |
|---|---|---|
| Test compound | Dose of the test compound (mg/kg) | Survival (%) |
| N-methyl- laurotetanine hydrochloride | 120 | 80 |
| | 60 | 40 |
| | 30 | 0 |
| None | 0 | 0 |

From the results of the above tests, it has been made clear that N-methyllaurotetanine, glaucine, boldine and their salts have much superior antiallergic effects without apomorphine-like side effect.

The following Examples are given to illustrate this invention, but this invention is not limited thereto.

EXAMPLE 1 (Tablet)

| | |
|---|---|
| N-Methyllaurotetanine | 100 g |
| Lactose | 200 g |
| Starch | 10 g |
| Magnesium stearate | 1 g |

The above ingredients are blended and compressed, in a conventinal manner, into 1,000 tablets weighing 330 mg, each of which contains 100 mg of the active ingredient. When desired, tablets thus obtained are coated with sugar-coating, film-coating or enteric-coating.

EXAMPLE 2 (Capsule)

| | | |
|---|---|---|
| Glaucine | 20 | g |
| Starch | 80 | g |
| Magnesium stearate | 0.3 | g |

The above ingredients are blended and divided into 1,000 parts, each of which is individually filled in hard-gelatin capsules in a conventional manner to give 1,000 capsules, each of which contains 20 mg of the active ingredient.

EXAMPLE 3 (Injection preparation)

Sterile hydrochloric acid salt of N-methyllaurotetanine (50 mg) was put into a sterile ampoule. When used, said active ingredient was dissolved into distilled water for injection (2 ml.)

We claim:

1. A method of inhibiting the symptoms of a histamine-type allergic reaction in a mammal in need thereof which comprises administering to said mammal, a non-toxic, effective amount of a compound of the formula:

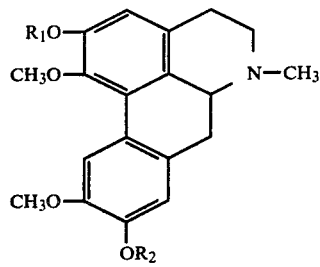

wherein $R_1$ and $R_2$ are each hydrogen or methyl, providing that when $R_1$ is hydrogen, $R_2$ is hydrogen; or a pharmaceutically acceptable acid addition thereof.

2. The method according to claim 1, in which the compound is glaucine.
3. The method according to claim 1, in which the compound is N-methyllaurotetanine.
4. The method according to claim 1, in which the compound is N-methyllaurotetanine hydrochloride.
5. The method according to claim 1, in which the compound is boldine.
6. A method of inhibiting histamine-release from mast cells in a mammal in need thereof which comprises administering to said mammal a non-toxic, effective amount of a compound of the formula:

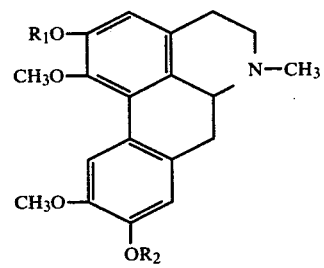

wherein $R_1$ and $R_2$ are each hydrogen or methyl, providing that when $R_1$ is hydrogen, $R_2$ is hydrogen; or a pharmaceutically acceptable acid addition salt thereof.

* * * * *